(12) United States Patent
Loerch (10) Patent No.: US 9,243,934 B2
(45) Date of Patent: Jan. 26, 2016

(54) AUTOMATIC CALIBRATION OF A MICROSCOPE SCANNING SYSTEM

(71) Applicant: MetaSystems Hard and Software GmbH, Altlussheim (DE)

(72) Inventor: Thomas Loerch, Altlussheim (DE)

(73) Assignee: MetaSystems Hard and Software GmbH (DE)

( * ) Notice: Subject to any disclaimer, the term of this patent is extended or adjusted under 35 U.S.C. 154(b) by 0 days.

(21) Appl. No.: 13/847,674

(22) Filed: Mar. 20, 2013

(65) Prior Publication Data

US 2013/0278941 A1 Oct. 24, 2013

(30) Foreign Application Priority Data

Mar. 20, 2012 (DE) .......................... 10 2012 005 587

(51) Int. Cl.

| | | |
|---|---|---|
| G01B 11/14 | (2006.01) | |
| G01D 5/347 | (2006.01) | |
| B01L 9/00 | (2006.01) | |
| G01N 33/53 | (2006.01) | |
| G02B 21/34 | (2006.01) | |
| G02B 21/36 | (2006.01) | |
| G01N 35/00 | (2006.01) | |
| G02B 21/26 | (2006.01) | |

(52) U.S. Cl.
CPC .............. *G01D 5/34715* (2013.01); *B01L 9/52* (2013.01); *G01N 33/5304* (2013.01); *G01N 35/00029* (2013.01); *G01N 35/00693* (2013.01); *G02B 21/34* (2013.01); *G02B 21/36* (2013.01); *B01L 2200/025* (2013.01); *B01L 2300/0822* (2013.01); *G01N 2035/00138* (2013.01); *G01N 2035/00851* (2013.01); *G02B 21/26* (2013.01)

(58) Field of Classification Search
None
See application file for complete search history.

(56) References Cited

U.S. PATENT DOCUMENTS

| | | |
|---|---|---|
| 5,428,690 A | 6/1995 | Bacus et al. |
| 5,581,487 A | 12/1996 | Kelly et al. |
| 5,694,212 A | 12/1997 | Weissman |
| 7,343,257 B2 | 3/2008 | Stock |
| 7,760,428 B2 | 7/2010 | Sieckmann |
| 2003/0012420 A1 | 1/2003 | Verwoerd et al. |
| 2003/0027342 A1 | 2/2003 | Sheridan et al. |
| 2005/0051614 A1 | 3/2005 | Albany |
| 2006/0279746 A1 | 12/2006 | Stock |
| 2007/0279735 A1* | 12/2007 | Sieckmann ............ 359/396 |
| 2010/0259805 A1 | 10/2010 | Osipchuk |

FOREIGN PATENT DOCUMENTS

| | | |
|---|---|---|
| CA | 2307287 | 4/1999 |
| DE | 10336803 | 3/2005 |
| DE | 102004031570 | 1/2006 |
| DE | 60034055 | 12/2007 |

* cited by examiner

*Primary Examiner* — Tri T Ton
(74) *Attorney, Agent, or Firm* — Onello & Mello, LLP (57) ABSTRACT

The invention provides a method for automatic calibration of slides and a method for automatic calibration of slide frames and a slide for performing the method. To this end, slide frames (4; 210) with at least one slide seat and slide (212a-212h; 300) are provided with a calibration marking (304). In particular the inventive slide (212a-212h; 300) includes a slide substrate (302) and a calibration marking (304), the calibration marking (304) being connected to the slide substrate (302).

16 Claims, 3 Drawing Sheets

AUTOMATIC CALIBRATION OF A MICROSCOPE SCANNING SYSTEM

CROSS-REFERENCE TO RELATED APPLICATIONS

This application claims the benefit, under 35 U.S.C §119, to German Patent Application No. 10 2012 005 587.0, filed on Mar. 20, 2012, in the German Patent and Trademark Office, the disclosure of which is incorporated herein in its entirety by reference.

FIELD OF INTEREST

The invention relates to a method for automatic calibration of slides, a method for automatic calibration of slide frames, and to a slide for performing the method "Method for Automatic Calibration of Slide Frames."

BACKGROUND

In general, slides are used for microscopy. For instance, cell or tissue specimens are applied to or positioned on a slide. The slide with the cell or tissue specimen is then placed on a microscope stage of a microscope so that the cell or tissue specimen may be examined with the microscope.

In addition, microscope scanning systems are used for automatically finding objects like cells in a tissue specimen that is positioned on a slide. These may be, for instance, cells with a certain property (e.g. a marking) that are present in a tissue slice that is on the slide. A marking may be for instance staining of a cell.

Microscope stages and scanning stages are equipped as measuring elements with coordinate systems so that, for instance, the position of the found object may be precisely determined using coordinates from the measuring element and/or slide.

As a rule the position of the found objects is stored. This may be done so that after a specimen (e.g. tissue specimen) on a slide has been scanned, the found objects (e.g. cells) can be automatically relocalized or reexamined, i.e. re-presented to the viewer for visual examination. An absolute X-Y-Z coordinate system is not necessary to guarantee precise relocalization as long as the relocalization takes place immediately after the specimen has been scanned, i.e. the specimen has not been removed from its original position on the scanning stage. In this case it is enough to approach the relative coordinates stored during the search.

In many cases it is not possible to relocalize immediately after the specimen has been scanned. This is especially the case when the scan is performed in "batch" mode. In this case, for instance, a certain number of specimens on the slides are automatically scanned first, e.g. overnight, and the found objects are not to be reviewed until the next morning.

In such a mode, it will regularly be necessary to remove the scanned slide from the stage using an automatic exchanger/robot module and to load a new set of slides. This is preferably not performed with individual slides, since direct manipulation of glass slides is prone to faults due to the normal tolerances of the slide dimensions. Instead, slides are placed into a frame (hereinafter referred to as a "slide frame"), which is then exchanged as a unit. Depending on size and configuration, one slide frame may accommodate one or a plurality of slides.

For receiving slides in a slide frame, corresponding slide seats are provided so that one slide may be placed into each slide seat.

The slide frames are stored for instance in a magazine, from which magazine the robot module can remove the slide frames. Once the slide(s) that is/are arranged in the slide frame has/have been scanned, the slide frame may be returned to the magazine.

In addition, specimen exchangers may be provided that have for instance 1 to 11 magazines, each magazine accommodating e.g. 16 slide frames, each with 5 slides. In order to be able to receive the slide or plurality of slides in one slide frame, the slide frames have one slide frame seat for each slide.

A 3-point self-centering support provides positioning accuracy for the slide frames themselves on the scanning stage.

The slide frames are not exactly identical; on the contrary, there are production tolerances. Although as a rule these production tolerances lead to positioning errors of a few tenths of a millimeter, this is still enough for instance to displace a cell out of the microscope image field when this cell is relocalized based on relative coordinates.

Consequently, the "absolute" coordinates for any position on a slide must be known for a slide frame in which the slide is arranged in order to be able to reliably relocalize any coordinates for an object that is mounted on the slide, regardless of the slide frame used and the slide frame receiving unit used.

In practice, it may happen that one slide is placed into successive different slide frames. For instance, one slide may contain a tissue specimen that was stained in order to mark a certain cell(s) with color. The slide is now placed into a "first" slide frame in order to scan the slide automatically. The stained cells are detected and their position on the slide is determined and stored. After this automatic scanning has concluded, the slide is removed from the "first" slide frame in order to destain the slide. Then the cells are stained again in order to obtain additional information about the cells to be examined. To this end, the slide is placed into a "second" slide frame and is again placed under the microscope for examination. It is necessary to be able to perform precise relocalization in order to be able to, immediately and in a simple manner, further examine the cells that were previously examined.

Therefore, for precise relocalization the position of a slide must be calibrated in each slide frame so that a slide may be placed into different slide frames and the positioning coordinates for a "found" object are accurate regardless of the slide frame used.

The same is true when a slide frame includes a plurality of slide seats. In this case, a calibration must be conducted for each slide seat so that the same slide may be placed into any slide seat of the slide frame and a "found" object can still be reliably relocalized.

In the past, calibration of a slide frame or a slide seat was performed such that a special slide (calibration slide) that was provided with a highly precise coordinate grid was placed into the slide seat that was to be calibrated. Then three defined coordinates (three calibration positions) that were covered with cross-hairs were approached in succession, and this was displayed in a live image on a monitor for the microscope scanning system. Software stored the coordinates for the scanning stage that belonged to these three calibration positions and the coordinates were used for converting coordinates between different positions on the slide with respect to the slide frame.

However, the current generation of specimen exchanger can include up to 880 slides, so that this approach to calibrating slide frames is no longer practical.

This is because it is necessary to perform a placement process for the calibration slide for each slide seat for a slide in a slide frame and it is also necessary to perform three precise manual positioning operations. Interactive centering of the three grid positions is time-consuming, as well. If these steps are to be skipped, a large number of identical calibration slides (for instance, 80 calibration slides) are needed to be able to automatically calibrate a magazine of slide frames. The costs for the high-precision calibration slides are a drawback in this process in accordance with the prior art, and the calibration precision is limited by the precision of the calibration slide. Producing calibration slides with tolerances of 1 to 5 µm is complex, and therefore expensive.

SUMMARY

It is therefore one object of the invention to provide a method that makes it possible to calibrate slide frames in a simpler and less expensive manner than the prior art methods permit.

It is furthermore an object of the invention to provide a slide that assures precise calibration of slide frames and at the same time is simpler and less expensive to produce than calibration slides known from the prior art.

This object is inventively attained using the features of the independent claims. Preferred embodiments of the invention are the subject-matter of the dependent claims.

One aspect of the present invention relates to a method for automatically calibrating slides that includes the following steps: providing a slide frame with at least one slide seat, positioning coordinates for the slide seat being established for a microscope scanning system; providing at least one slide with a calibration marking; arranging the at least one slide in the at least one slide seat for the slide frame; arranging the slide frame with the slide on a scanning stage for the microscope scanning system; detecting marking coordinates for the calibration marking based on detecting the calibration marking for the slide using the microscope scanning system; and detecting a deviation between the positioning coordinates for the slide seat and the marking coordinates for the slide.

The slide frame is in particular a slide frame that has already been calibrated. If a calibrated slide frame includes a plurality of slide seats, the term "calibrated slide frame" shall be understood to mean that each of its slide seats is calibrated.

When a slide frame includes several or a plurality of slide seats, a slide may be placed or arranged in at least one (desired) slide seat in order to calibrate this slide.

The term "slide seat" shall be construed in particular as a position for a slide in or on a slide frame. The term "slide seat" also includes an area of a slide that can be placed in a slide frame and scanned or examined using a microscope.

In other words, a calibrated slide frame has already been measured such that the absolute positioning coordinates for a slide that is placed into this slide frame or into a slide seat have already been measured or are known. Therefore, using the absolute positioning coordinates it is possible to establish for instance a coordinate origin, center point, and/or scannable area of the slide, that may be approached or scanned by inputting scanning stage coordinates for a microscope scanning system.

In particular the positioning coordinates for the slide seat, which the calibrated slide frame includes, are known. These positioning coordinates may for instance match a coordinate origin and/or a center point for an inserted slide. This center point does not have to be the geometric center point based on the outer dimensions of the slide; on the contrary, it may also be a center point that corresponds to a center point of the scannable area or scanning window established by the slide seat.

In addition, the positioning coordinates for the slide seat may establish a scannable area or scanning window for an inserted slide with respect to the microscope scanning system.

The positioning coordinates for the slide seat may in particular establish an orientation or positioning of the slide seat or of the slide placed into the slide seat with respect to the microscope scanning system. The positioning coordinates for the slide seat may also contain or be the same as positioning coordinates for the slide placed into the slide seat.

For instance, a scanning stage may be adjusted according to the positioning coordinates for the slide seat in order to scan a slide and/or to relocalize an object that was already found.

The positioning coordinates may in particular be coordinates in a Cartesian coordinate system. In other words, the positioning coordinates may contain X and Y coordinates for one or a plurality of points on the slide seat. In addition, positioning coordinates may also contain Z coordinates for one or a plurality of points with respect to the slide seat. The positioning coordinates may where necessary be converted by means of transformation information so that (a) specific positioning coordinate(s) is/are converted to a position/orientation of a scanning stage.

The positioning coordinates and the transformation information may be stored for instance in a storage medium that can be read by the microscope scanning system.

In accordance with the method, a slide with a calibration marking may be arranged or placed into a calibrated slide frame, this slide not yet being calibrated. The calibrated slide frame with the slide (to be calibrated) is arranged on a scanning stage for the microscope scanning system.

The calibration marking may include at least one point, at least one cross, or at least one line. The microscope scanning system detects the calibration marking by scanning. The calibration marking is preferably detected or optically detected automatically by the microscope scanning system. In other words, the calibration marking for the slide is detected by the microscope scanning system. Image recognition may be used for this, for instance.

Based on the detection of the calibration marking, the microscope scanning system detects marking coordinates for the calibration marking. These marking coordinates are especially X-Y coordinates for one or a plurality of points on the calibration marking. These marking coordinates are also Z coordinates, which define a focus position.

The marking coordinates may be relative coordinates based on a coordinate origin for the calibrated slide frame or slide seat. Alternatively or in addition, the marking coordinates may contain the coordinates for the scanning stage or the measuring device for the scanning stage.

For calibrating the slide with the calibration marking, the deviation between the marking coordinates for the slide and the positioning coordinates for the calibrated slide seat is detected.

In other words, the deviation is a distance between the marking coordinates and the positioning coordinates.

The deviation is a relative variable for the marking coordinates with respect to the positioning coordinates for the (calibrated) slide seat, the positioning coordinates for the (calibrated) slide seat being "absolute" positioning coordinates.

The deviation may be based on an evaluation of the measurement data for the scanning stage. For instance, a scanning stage may approach the calibration marking, preferably automatically, and detect the marking coordinates as $X_1$ and $Y_1$ coordinates. The marking coordinates correspond to the $X_1$ and $Y_1$ coordinates of the measuring system for the scanning stage.

In another step, the positioning coordinates, for instance, are then read as $X_2$ and $Y_2$ coordinates for the (calibrated) slide seat that were stored e.g. in a storage medium. Where necessary, the positioning coordinates that are read out may be converted with respect to a measuring scale for the scanning stage.

Differences $\Delta x$ and $\Delta y$ between the marking coordinates $X_1$ and $Y_1$ and the positioning coordinates $X_2$ and $Y_2$ are calculated. Alternatively, these differences may be determined in that the measuring system is adjusted to zero when the marking coordinates $X_1$ and $Y_1$ are approached.

This calculated or determined difference is stored or established as the deviation so that the deviation for the slide with the calibration marking may be queried when needed.

In other words, if the deviation was detected in a Cartesian coordinate system, the deviation indicates a distance in the X direction and a distance in the Y direction of a marking coordinate for the calibration marking from a corresponding positioning coordinate. It is also possible for other coordinate systems to be used.

Thus the importance of calculating a difference between measured coordinates for the markings and the positioning coordinates for the slide seat is attached in particular to detecting a deviation.

In particular the term "detecting a deviation" shall also be construed to mean allocating the deviation detected for a specific slide to this specific slide. In other words, the detected deviation is accurate for this one slide with the calibration marking.

In summary, a slide that has a calibration marking and for which a deviation has been detected is a calibrated slide.

The deviation preferably includes one or a plurality of deviation coordinates.

In particular, the deviation coordinates for the slide may be deviations from positioning coordinates for different points that were established for a slide seat.

For instance, four corner points on the slide seat may have been established as positioning coordinates, X-Y coordinates having been defined for each cornerpoint. In this case, deviation coordinates from the positioning coordinates for each corner point may be detected or established. In other words, one deviation may contain a plurality of deviation coordinates for different points that are defined by positioning coordinates.

Preferably, the deviation coordinates can establish a deviation between the marking coordinates and the positioning coordinates, the deviation coordinates establishing a maximum scannable scanning area for the slide. For instance, a scanning area may be established by at least three points, deviation coordinates being detected for each point.

Alternatively or in addition, the deviation coordinates can establish a deviation between the marking coordinates and the positioning coordinates, the deviation coordinates establishing a center point for the slide.

Furthermore, alternatively or in addition, the deviation coordinates can establish a deviation between the marking coordinates and the positioning coordinates, the deviation coordinates establishing at least two reference points that establish a conversion of coordinates for the slide seat with respect to coordinates for the scanning stage for the microscope scanning system.

The method furthermore preferably includes the step: storing the detected deviation in a storage medium that may be connected to the slide.

The storage medium is preferably a barcode. The storage medium may also be an RFID label.

As a rule, a deviation that has been detected for a specific slide is accurate only for this slide. Therefore, it is necessary to reliably allocate the deviation detected for a specific slide to this slide. The slide may preferably be reliably allocated to its deviation using a "physical" allocation of the slide to a storage medium in which the detected deviation is stored. For instance, the detected deviation may be stored in a barcode that acts as the storage medium, the barcode being connected to the slide. Similarly, an RFID (radiofrequency identification) label may be used instead of or in addition to a barcode.

The stored and detected deviation may be read out of the storage medium by means of a reading device (e.g. barcode or RFID reader). The reading device may be for instance connected or connectable to the microscope scanning system. Alternatively, a reading device may be connectable to a computer and the computer may then be connectable to the microscope scanning system.

In addition, the slide may include an identifier, such as for instance a number or a barcode. The deviation may be stored together with a link to the identifier or together with the identifier in a storage medium that is not physically connected to the slide. For instance the storage medium may be arranged in a computer. The allocation of deviation to slide is assured by the identifier.

The detected deviations may be provided to the microscope or transferred thereto via an interface on the microscope scanning system, for instance.

The calibration marking preferably includes one or a plurality of lines and/or points.

In particular the lines may be arranged such that the lines intersect one another. In other words the lines provides crossings or intersecting points. One or a plurality of such intersecting points may be used as calibration markings, for instance.

Furthermore, the calibration marking is preferably applied to a transparent carrier material. The transparent carrier material may be detachably connected to the slide. The transparent carrier material is preferably an adhesive film.

The adhesive film may advantageously be applied rapidly and simply to a slide, such as for instance a glass slide. Thus, in general, any desired slide may be used.

In another embodiment, the calibration marking is applied directly to the slide, such as for instance printed and/or lasered thereon. Likewise, the calibration marking may be added to or embedded in the slide. For instance the calibration marking may be a fiber or thread that is embedded in the slide.

In addition, the calibration marking is preferably applied by printing on the slide. Alternatively or in addition, the calibration marking may be applied by printing on the transparent carrier material.

The slide frame furthermore preferably includes a plurality of slide seats, one slide with one calibration marking being placed into or being able to be placed into each slide seat. Thus one deviation may be detected for each slide that is arranged in the slide frame.

Several or a plurality of slides that have been provided with an inexpensively produced calibration marking may advantageously be automatically calibrated one after the other in this way.

The method described in the foregoing for automatic calibration of a slide advantageously permits calibration of inexpensive slides, high precision for the calibration marking on the slide not being necessary compared to the calibration slides with highly precise coordinate grids known from the prior art.

One aspect of the present invention relates to a method for automatically calibrating slide frames that includes the steps: providing at least one slide with a calibration marking, a deviation between absolute positioning coordinates for the slide and the calibration marking for the slide being established; arranging the slide in a slide seat for a slide frame; arranging the slide frame with the slide on a scanning stage for a microscope scanning system; detecting marking coordinates for the calibration marking for the slide based on detecting the calibration marking for the slide using the microscope scanning system; and establishing corrected positioning coordinates for the slide seat for the slide frame based on the marking coordinates and the deviation.

The slide frame is in particular a non-calibrated or an inadequately calibrated slide frame. In other words, objects on a slide that is placed into a non-calibrated or only inadequately calibrated slide frame may be relocalized only poorly or inadequately. Accordingly, it is not possible, or it is only possible to a limited extent, to review slides that are placed into such an inadequately calibrated slide frame using automatic scanning.

If a non-calibrated slide frame includes a plurality of slide seats, the term "non-calibrated slide frame" shall be construed to mean that at least one or even each of these slide seats is/are non-calibrated.

The term "slide seat" shall be construed in particular to mean a position of a slide in or on a slide frame. The term "slide seat" also includes a scannable area or an area that can be examined by microscope, which area is in a slide that may be placed into a slide frame.

In other words, with a non-calibrated slide frame it is not assured that the absolute positioning coordinates for a slide that is placed into this slide frame are accurate or match the actual positioning coordinates for the slide frame on the scanning stage. It may be that a correction or adaptation of the absolute positioning coordinates for the slide to the positioning coordinates for the (non-calibrated) slide frame is necessary.

An accurate coordinate origin, center point, and/or scannable area for the slide relative to the slide frame is therefore not assured.

On the contrary, the slide may be displaced with respect to the scannable area or the area that can be examined under a microscope because there is an unknown difference between the known absolute positioning coordinates for the slide and the actually required coordinates that would have to be adjusted on the scanning stage with respect to the slide frame.

Inputting scanning stage coordinates for an object on a slide that is not placed in this non-calibrated slide frame may lead to no object or to the wrong object.

In addition, there is no mechanical origin that establishes an "absolute" coordinate system. On the contrary, "absolute coordinates" or "absolute positioning coordinates" are established practically after (every) assembly of a (scanning) stage on the microscope in that a precise calibration slide (e.g. micropositioner from Berliner Glas) is placed into a slide seat for a slide frame and three predefined markings on the calibration slide are successively centered under the microscope lens (with visual control through the eyepiece). The associated stage coordinates are stored and used for determining an absolute coordinate system.

Based on such an (established) "absolute coordinate system," slide seats for slide frames may be calibrated by means of the method for automatic calibration of slide frames.

In other words, slides to be calibrated or slide frames to be calibrated are calibrated relative to this absolute coordinate system.

In particular, the concept "absolute coordinates" or "absolute positioning coordinates" should be construed to mean established positioning coordinates for a calibrated slide that establish or determine a specific position in the absolute coordinate system. In particular absolute positioning coordinates "align" or "center" a slide based on these absolute positioning coordinates.

The absolute positioning coordinates for a calibrated slide are known or were already established. These absolute positioning coordinates may establish or define for instance a coordinate origin and/or a center point for the slide. Moreover, the absolute positioning coordinates for the slide may establish a scannable area or scanning window for the slide in the microscope scanning system. The absolute positioning coordinates for the slide may in particular establish an alignment or positioning of the slide with respect to the microscope scanning system. The absolute positioning coordinates for the slide seat may contain or be positioning coordinates for a calibrated slide seat or a slide frame.

The absolute positioning coordinates are especially the positioning coordinates that were established for a specific calibrated slide as this slide was arranged in the calibrated slide seat in order to establish/detect the positioning coordinates. The positioning coordinates for the now calibrated slide were preferably detected or established by means of the method for automatic calibration of slides.

The absolute positioning coordinates may in particular be coordinates in a Cartesian coordinate system. In other words, the absolute positioning coordinates may contain X and Y coordinates for one or a plurality of points on the slide.

In addition, the absolute positioning coordinates may also contain Z coordinates.

The absolute positioning coordinates may be converted where necessary by means of transformation information so that (a) specific positioning coordinate(s) is/are converted to a setting/alignment or measurement scale for a scanning stage. The absolute positioning coordinates and the transformation information may be stored for instance in a storage medium that can be read by the microscope scanning system.

In accordance with the method, a slide with a calibration marking is arranged in or placed into a non-calibrated slide frame, the slide being calibrated with a calibration marking. The non-calibrated slide frame with the (calibrated) slide is arranged on a scanning stage for the microscope scanning system.

The calibration marking may include at least one point, at least one cross, or at least one line. The calibration marking is detected by scanning conducted by the microscope scanning system. The calibration marking is preferably automatically detected or optically detected by the microscope scanning system. In other words, the microscope scanning system detects the calibration marking for the slide.

The microscope scanning system detects marking coordinates for the calibration marking based on the detection of the calibration marking. These marking coordinates are in particular X-Y coordinates for one or a plurality of points in the calibration marking. Other coordinate systems may be used instead of Cartesian coordinates. In particular marking coordinates may contain Z coordinates in addition to the X-Y coordinates.

The marking coordinates may contain the coordinates for the scanning stage or the measuring device for the scanning stage.

For calibrating the slide frame, corrected positioning coordinates are established that are determined starting with the marking coordinates for the slide and the deviation.

In other words, the absolute positioning coordinates for the slide should agree with the corrected positioning coordinates for the slide frame or the slide seat. In order to be able to attain this agreement, it is first necessary to approach the calibration marking. In this way the X-Y coordinates for the scanning stage may be found with respect to the calibration marking. These X-Y coordinates for the scanning stage are detected as marking coordinates. Thus, the positioning of the calibration marking in the slide frame is known or established.

In the next step the correct positioning of the slide frame or the correct adjustment for the scanning stage may then be determined. To this end, a corrected positioning of the slide frame is established based on the known distance or deviation of the absolute positioning coordinates (e.g. center point of the slide, etc.) from the calibration marking/marking coordinates. For instance, the deviation may be approached or adjusted proceeding from the marking coordinates with the scanning stage so that then the adjustments (X and Y coordinates and Z coordinates, where necessary, for a focus position) of the scanning stage are known that actually match or are congruent with the points that are defined by the absolute positioning coordinates for the slide.

Alternatively or in addition, the corrected positioning coordinates may be computed based on the marking coordinates, taking the deviation into account.

The deviation is a relative variable for the marking coordinates with respect to the absolute positioning coordinates of the calibrated slide. The points that are established by the corrected positioning coordinates of the calibrated slide seat are congruent with the points that are established by the absolute positioning coordinates for the slide.

Preferably the (established) deviation/distance between the absolute positioning coordinates for the slide and the calibration marking for the slide corresponds to the detected deviation between the marking coordinates of the calibration marking for the slide and the positioning coordinates for a (calibrated) slide seat that was detected or determined during the method for automatic calibration of slides. Consequently the (established) deviation is used during calibration of the slide seat in order to establish or calculate the precise, that is, the corrected, positioning coordinates based on the marking coordinates of the calibration marking.

The corresponding X and Y coordinates in the measuring system of the scanning stage with respect to the corrected positioning coordinates are detected for a slide frame or a slide seat. The slide frame or slide seat is thus calibrated.

The aforesaid explanation regarding the deviation also applies with respect to this method for calibration of slide frames.

In particular the term "establishment of corrected positioning coordinates" shall also be construed to mean allocation of the established corrected positioning coordinates for a specific slide frame or slide seat to this specific slide frame or slide seat. In other words, the established corrected positioning coordinates apply only for this one slide frame or slide seat.

In summary, a slide frame or slide seat for which corrected positioning coordinates are or have been established is a calibrated slide frame or slide seat.

In another step, the corrected positioning coordinates for the (calibrated) slide seat for example, which coordinates were stored, e.g., in a storage medium, are then read out in order to scan another slide or in order to relocalize objects on this slide.

The corrected positioning coordinates for the slide seat preferably establish a maximum scannable scanning area for a slide that may be arranged in the slide seat.

In particular, the corrected positioning coordinates for the slide seat may be positioning coordinates for different points that were established for a slide that may be placed therein. For instance, four corner points for a slide may be established as absolute positioning coordinates, X-Y coordinates having been defined as absolute positioning coordinates for each corner point. In this case, corrected positioning coordinates may be detected or established for the absolute positioning coordinates of each corner point starting from the marking coordinates. In other words, corrected positioning coordinates may contain a plurality of positioning coordinates for different points that are defined by corrected positioning coordinates that are different from one another.

Alternatively or in addition, the corrected positioning coordinates for the slide seat may establish a center point for a slide that can be arranged in the slide seat. For instance, a scanning area may be established by at least three points, corrected positioning coordinates being determined for each point.

Further, alternatively or in addition, the corrected positioning coordinates for the slide seat may establish at least two reference points that establish a conversion of coordinates for a slide that can be arranged in the slide seat with respect to coordinates for the scanning stage of the microscope scanning system.

The method preferably also includes the following step: storing the corrected positioning coordinates on a storage medium that is preferably connected to the slide frame, the storage medium preferably being a barcode or an RFID label.

The storage medium is preferably a barcode. The storage medium may furthermore be an RFID label.

As a rule, corrected positioning coordinates that were detected for a specific slide frame or slide seat apply only to this slide frame or slide seat. Consequently it is necessary to reliably allocate the corrected positioning coordinates established for a specific slide frame or slide seat to this slide frame or slide seat.

Preferably, reliable allocation of slide frame or slide seat to its corrected positioning coordinates occurs using a "physical" allocation of slide frame or slide seat to a storage medium in which the corrected positioning coordinates are stored. For instance, the corrected positioning coordinates may be stored in a barcode that is used for the storage medium, the barcode being connected to the slide frame or slide seat. Likewise, an RFID label (radio frequency identification label) may be used instead of or in addition to a barcode.

The stored or established corrected positioning coordinates may be read out of the storage medium by means of a reader device (for instance a barcode or RFID reader device). The reader device may for instance be connected to the microscope scanning system or may be connectable thereto. Alternatively, a reader device may be connectable for instance to a computer and the computer may then be connectable to the microscope scanning system.

Furthermore, the slide frame or slide seat may include an identifier, such as for instance a number or a barcode.

In particular a barcode may have a 1D code (one-dimensional code) and/or 2D code (two-dimensional code). For instance, a 1D code may be designed like a conventional commercial barcode. A conventionally used and accessible commercial barcode is for instance an EAN (European Article Number) or a UPC (Universal Product Code).

The corrected positioning coordinates may be stored together with a link to the identifier or together with the identifier in a storage medium that is not physically connected to the slide frame. For instance, the storage medium may be arranged in a computer. The identifier assures corrected positioning coordinates are allocated to the specific slide frame. If a slide frame has a plurality of slide seats, each slide seat may be allocated via a corresponding identifier or directly via the corrected positioning coordinates. For instance, the detected corrected positioning coordinates may be made available to the microscope scanning system or transferred thereto via an interface on the microscope scanning system.

The calibration marking preferably includes lines and/or points.

In particular, the lines may be arranged such that the lines intersect one another. In other words, the lines provide intersections or intersecting points. One or a plurality of such intersecting points may be used for instance as a calibration marking.

Furthermore, the deviation is preferably also stored in a storage medium, and the deviation may be read out from this storage medium so that corrected positioning coordinates may be established in a simple manner. The deviation is advantageously machine-readable so that corrected positioning coordinates may be calculated or determined automatically.

The method furthermore preferably includes the step: reading a storage medium that is connected to the slide and in which the deviation is stored.

In this case the deviation is advantageously immediately available when the slide is used because the storage medium and the slide are connected to one another.

This also advantageously prevents a deviation from being incorrectly allocated to a different slide and therefore to the wrong slide, which would lead to incorrect or incorrectly corrected positioning coordinates.

The slide frame preferably includes a plurality of slide seats, a slide with a calibration marking being placed into each slide seat in order for corrected positioning coordinates to be established for each slide seat.

Several or a plurality of slide seats may advantageously be automatically calibrated one after the other in this manner.

The method described in the foregoing for automatic calibration of a slide frame advantageously permits a slide frame to be calibrated based on inexpensive slides that are simple to produce.

One or a plurality of the method steps for the method for automatic calibration of a slide may advantageously be used in combination with one or a plurality of method steps for the method for automatic calibration of a slide frame. In particular the two methods may be performed in combination.

One aspect of the present invention relates to a slide including: a slide substrate and a calibration marking, the calibration marking being connected to the slide substrate, and the slide being suitable for performing a calibration in accordance with any of the methods for calibrating slide frames described in the foregoing.

A slide substrate is preferably a glass or plastic plate that is normally used as a slide in microscopy.

The calibration marking preferably includes one or a plurality of lines and/or points. In addition, the calibration marking is preferably applied to a transparent carrier material. In another preferred embodiment, the calibration marking is printed onto the transparent carrier material.

The calibration marking preferably includes at least two automatically detectable features that establish at least two (reference) coordinates or permit the establishment of such (reference) coordinates.

The transparent carrier material is preferably a film. The transparent material is preferably connected to the slide substrate in a material fit. The transparent carrier material may be designed as an adhesive film that is glued to the slide substrate.

In other words, a glass slide may have a transparent adhesive film glued to it.

In summary, the fully automatic calibration of slide frames is based on calibration slides that are simple and inexpensive to produce and that contain automatically detectable markings.

Thus, the interactive centering of the three grid positions that is normally used in the prior art is advantageously not used. The second interactive step of placing the calibration slide into the next slide seat in accordance with the prior art also advantageously becomes superfluous.

It is also advantageously unnecessary to provide a high number of identical calibration slides (for instance 80) to be able to automatically calibrate a magazine with slide frames in accordance with the prior art. A drawback of this method according to the prior art is the cost for very precise calibration slides, the precision of the calibration being limited by the precision of the calibration slides. Producing calibration slides with tolerances of 1 to 5 µm is prohibitively expensive.

The present methods are, in particular, advantageous when a plurality of slide frames and slide seats are to be calibrated. In this case it is possible in particular to save a great deal of time compared to prior art methods.

In addition, the present methods are also advantageous when an automatic scanning system has more than a single position for a slide. In other words, the inventive methods and the inventive slides are advantageous when slide frames with a plurality of slide seats are used and/or a plurality of slide frames are used and it must be assured that it is possible to precisely relocalize objects when the slides used are not always placed into the same slide seats. In other words, the inventive methods and the slide are advantageous when reliable relocalization of an object on a slide is to be assured in different slide seats.

The statements, descriptions, and definitions provided for the aforesaid methods also apply to the inventive slide in terms of its configuration and use.

BRIEF DESCRIPTION OF THE DRAWINGS

The invention shall be described in greater detail in the following using exemplary embodiments and referring to the attached drawings for examples. In particular individual features of the aspects and/or embodiments described in the foregoing and/or in the following may be omitted from the aspect and/or the embodiment or may be combined to create additional embodiments.

DETAILED DESCRIPTION OF PREFERRED EMBODIMENTS

Figure 1:
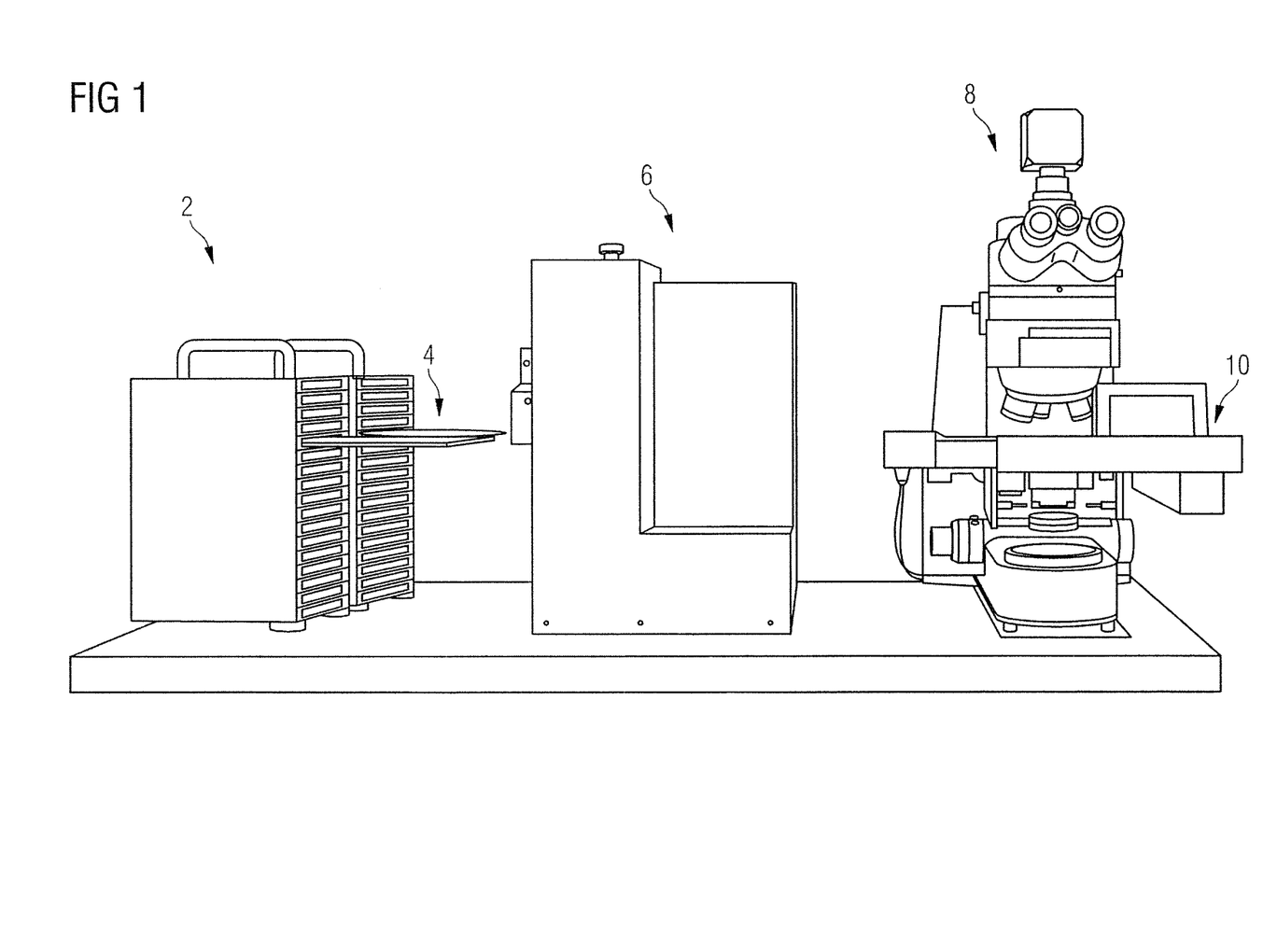
FIG. 1 depicts a microscope scanning system.

FIG. 1 depicts a microscope scanning system 100 that includes a magazine 2, a robot module 6, and a scanning microscope 8 with a scanning stage 10.

The magazine 2 includes a plurality of slide frames 4, for instance 16 slide frames 4. A slide frame 4 may be removed from the magazine 2 and arranged or positioned on the scanning microscope 8 by means of the robot module 6.

For instance, one slide frame 4 may be arranged or positioned on the scanning microscope 8. To this end, the robot module 6 removes one slide frame 4. Each slide frame 4 may include five slide seats, for instance, into each of which one slide may be placed or inserted or arranged. The slides may in particular be placed or oriented therein location-fast. For instance, slides could be arranged on/in the slide frames by means of magnetic attachment or positive fit placement or orienting devices. In other words, it can be assured by means of a suitable attachment that slides are always positioned or arranged the same way on a slide frame so that good reproducibility is assured in terms of positioning slides on the slide frame.

Figure 3:
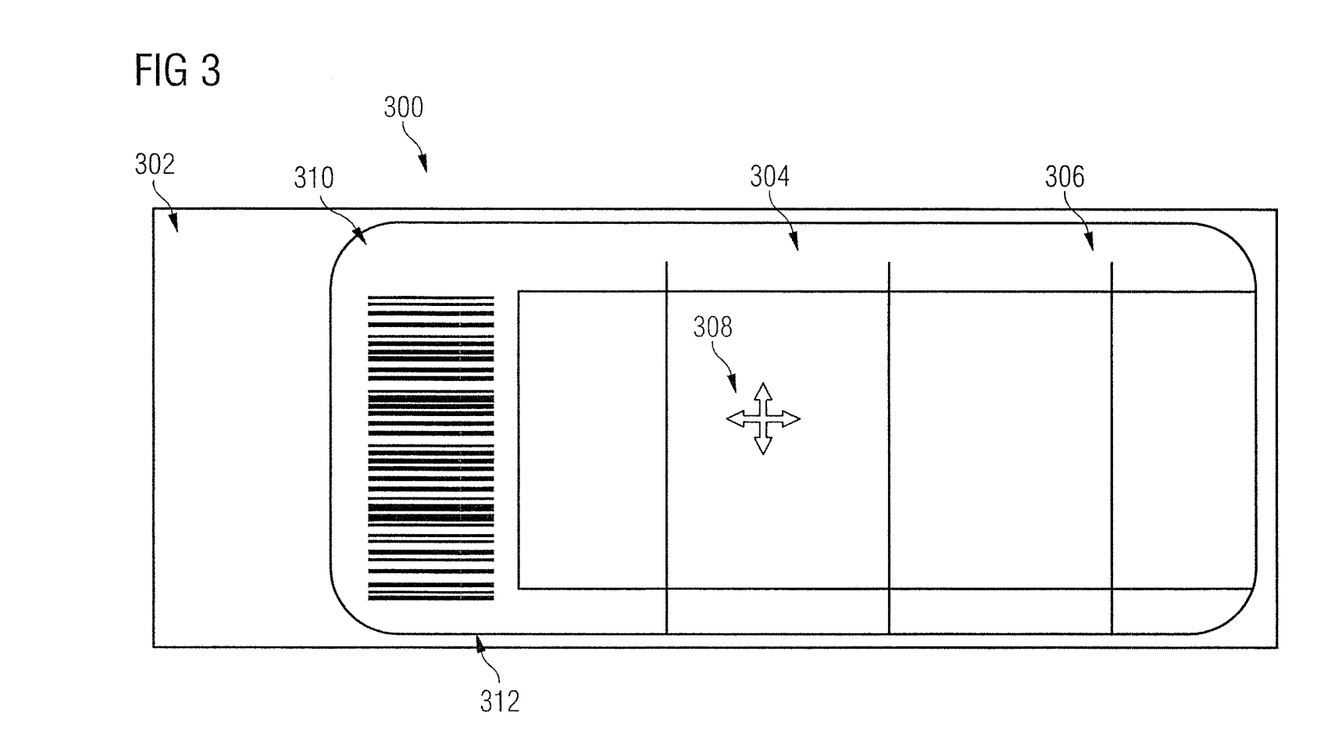
FIG. 3 depicts a slide with a calibration marking.

For automatic calibration of slides, the robot module 6 may remove, for instance, a calibrated slide frame 4 with a slide seat from the magazine 2 and arrange it on the scanning stage 10 of the scanning microscope 8. The slide frame 4 is calibrated such that positioning coordinates for the slide seat are established for a microscope scanning system. Arranged in the slide seat is for instance a non-calibrated slide that is provided with a calibration marking. Such a slide is, for instance, comparable to the slide 300 as depicted in FIG. 3 and described in the following.

For calibrating this slide 300 with a calibration marking 304, the calibration marking 304 for the slide 300 is detected using the microscope scanning system 100, especially by the scanning microscope 8. The scanning microscope 8 detects or recognizes the calibration marking 304 and at the same time detects marking coordinates for this calibration marking 304. These marking coordinates may be measurement coordinates for the scanning stage 10.

The calibration marking 304 or its marking coordinates may not match the positioning coordinates for the calibrated slide seat. In other words, the point(s) that establish(es) or define(s) the marking coordinates is/are not congruent with or identical to the point(s) that establish(es) or define(s) the positioning coordinates. In this case, the (coordinate) adjustments for the scanning stage 10 for the marking coordinates differ from those for the positioning coordinates. Thus, there is a difference or deviation between the positioning coordinates for the slide seat and the marking coordinates for the slide 300.

For calibrating the slide 300, this deviation 308 or the distance between the calibration marking 304 for the slide 300 and the positioning coordinates for the slide seat is detected or determined.

For instance, if a center point was established using the positioning coordinate for the slide seat, center point coordinates for the slide 300 may be found for instance by adding the marking coordinates and the deviation.

In one method for automatic calibration of slide frames, a slide 300 calibrated according to the method described in the foregoing is used.

This slide 300 or a plurality of such slides 300 may be placed into a plurality of non-calibrated slides or slide seat(s). For automatic calibration, a robot module 6 may remove these non-calibrated slide frames that have been placed in a magazine 2 and place or position them on the scanning stage 10 of the scanning microscope 8.

The scanning microscope 8 detects the calibration marking 304 for instance by scanning the slide 300. The adjustments for the measuring device for the scanning stage 10 or the scanning stage coordinates are detected or established as marking coordinates.

In the next step for calibration of the slide seat, new positioning coordinates, that is, corrected positioning coordinates, for the slide seat are established. To this end, the deviation 308 determined with the previous method is added to the detected marking coordinates or the marking coordinates are changed in accordance with the deviation 308 so that special positioning coordinates that are correct for the slide seat are established.

Figure 2:
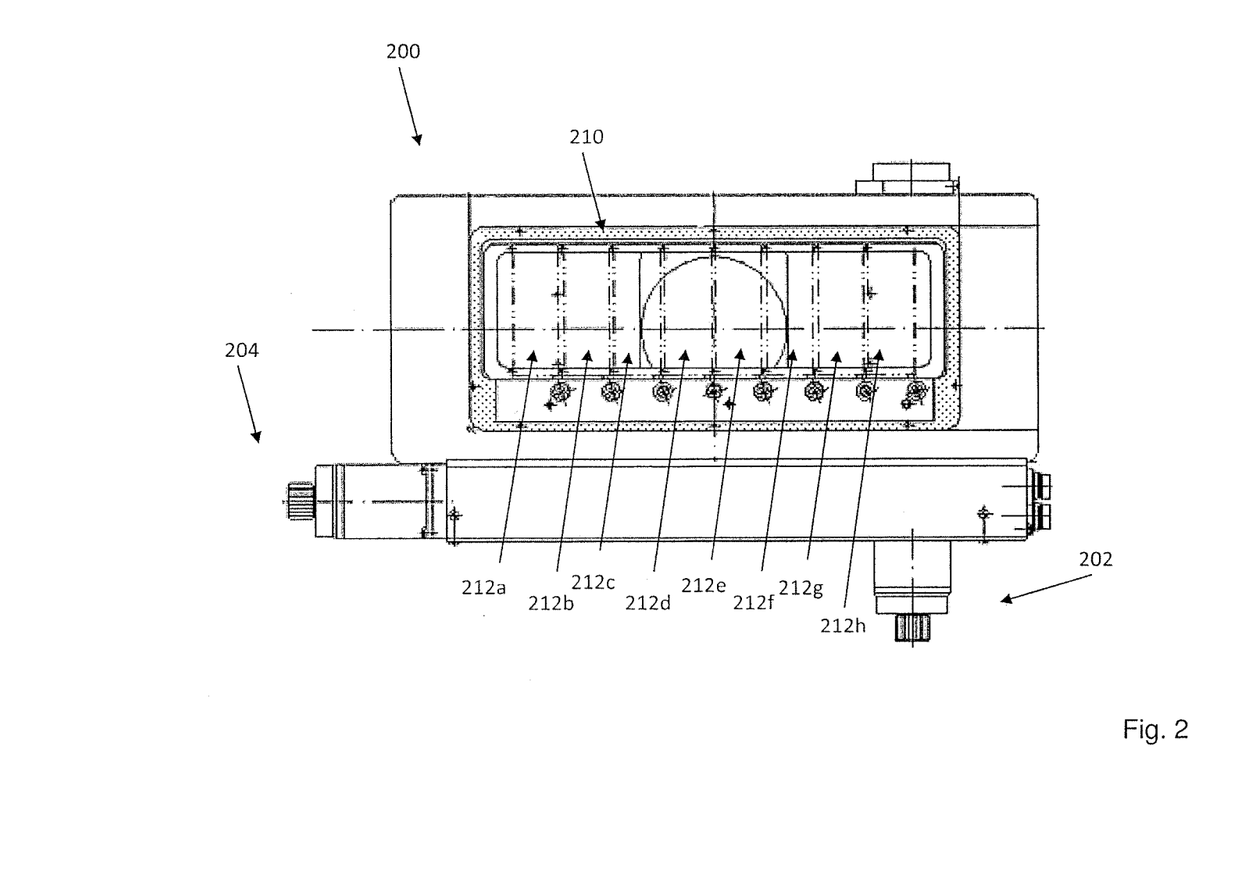
FIG. 2 is a schematic depiction of a scanning stage with a slide frame and eight slides placed therein.

FIG. 2 is a schematic depiction of a scanning stage 200 with a slide frame 210 and eight slides 212*a* through 212*h* placed therein. The scanning slide 200 furthermore includes a measuring device or motors for X-Y displacement 202, 204 with which the scanning stage 200 may be adjusted or moved. In particular by adjusting the measuring device 202, 204 the scanning stage 200 may be moved in an X direction and in a Y direction so that specific X and Y coordinates may be approached. In addition, Z coordinates may be adjusted using an autofocus function. For instance, objects that are positioned on a slide and to which object positioning coordinates have been assigned may be relocalized or approached by adjusting the X and Y coordinates and, where necessary, the Z coordinates.

It should be noted that the focus position may also be detected when calibrating or detecting an object. This may be done using an autofocus function. This can ensure that when an object is relocalized it appears somewhat "in focus" (at least near enough to a "correct" focus plane that an autofocus program brings the object into the "perfect" focus plane with a "relatively small lock-in range."

In one preferred embodiment, X, Y, and Z coordinates are always detected.

FIG. 2 schematically depicts, in particular, a scanning stage 200 for eight slides 212*a* through 212*h* (for instance manufactured by Märzhäuser, Wetzlar) having a fixed slide frame 210. This slide frame 210 may be 273 mm×116 mm, for instance. In an exchanger system having a robot module, an adapter frame is screwed in instead of the fixed slide frame; the adapter frame has three centering pins on which the exchange frame (e.g. slide frame) with corresponding bearing elements is placed, the bearing elements comprising one fixed bearing and two loose bearings (one with two degrees of translational freedom and one with three degrees of translational freedom). Such bearings are known, e.g., from adjustable mirror mountings. This assures precise reproducibility of the slide frame position (certainly less than 5 μm).

FIG. 3 depicts a slide 300 including a slide substrate 302, a calibration marking 304, and a storage medium 310. The slide substrate 302 may be a glass or plastic plate that is normally used in laboratories. The calibration marking 304 may comprise a plurality of intersecting lines or a grid, as illustrated.

Alternatively or in addition, one or a plurality of points may be provided as a calibration marking on or at the slide 300. Moreover, a diamond pattern and/or crosses may be provided as calibration markings. In particular, combinations of various lines and/or points or patterns may be used as calibration markings, as long as the calibration marking is reliably detectable and it is possible to detect marking coordinates.

In particular, it is possible for only some or only certain points for the calibration marking to be used for the calibration marking. For instance, only one or a plurality of intersecting points 306 may be used as a calibration marking 304.

In a calibrated slide 300, an intersecting point 306 was used for instance as a calibration marking so that a deviation 308 between this intersection point 306 and a center point of the slide 300 could be established proceeding from this intersection point 306. The deviation 308 is, in particular, a distance from the intersecting point 306 and may be detected as ΔX and Δy coordinates (relative coordinates).

In particular, a possible change to the focus position may be detected as the deviation 308, the change in the focus position being detected as Δz coordinates (relative coordinates).

This deviation 308 may be stored for instance in the storage medium 310 so that it may be read immediately. Alternatively, the storage medium 310 may be an identifier for the slide and reading the storage medium 310 may access a file in which the deviation 308 is stored. As shown in FIG. 3, the storage medium 310 may be a barcode.

The calibration marking 304 is, for instance, printed together with the barcode on a transparent carrier material 312 when the barcode 310 is used as an identifier. The transparent carrier material 312 may be an adhesive film.

In other words, a more cost-effective calibration slide 300 or slide 300 for calibrating slide frames is produced from one slide substrate 302 in that a label 312 with line numbers 304 is glued to the slide substrate 302. The barcode 310 represents the allocation of the calibration slide to the file with the measurement results (deviation 308 from measured position of characteristic intersecting points to expected "perfect" position).

Thus, in accordance with the invention, a calibration slide 300 is produced with simple means and is then precisely measured.

In summary, the calibration marking 304 may be printed on labels (as an exemplary carrier material 312) using a laser printer, for instance. These labels are then glued onto corresponding slide substrates 302. Then each of the slides 300 with a calibration marking 304 (calibration slide) is first individually measured. This is accomplished fully automatically using a slide frame that has already been calibrated or an exchanger system. The line intersections or crosses or points, etc., used for the calibration are detected automatically and their coordinates are stored in an individual calibration file. After any slide 300 (calibration slide) has been calibrated, a barcode 310 is applied that contains the measured deviation 308 or deviation coordinates from the marked positions (calibration marking) or indicates the file that contains this information.

In particular, the labels may be transparent or non-transparent, the term "non-transparent" being construed to mean that the non-transparent label is not permeable for ambient light (natural light or visible light) or is only "slightly" permeable. In particular, ambient light (possibly from a desk lamp) may be used reflecting from the non-transparent label.

During new calibration of slide frames or an exchanger system, all slide frames (calibration slide positions)—for instance 16 slide frames per magazine with five slide seats (slide positions) per slide frame—are fitted with previously calibrated slides 300 (measured calibration slides). In the now following automatic calibration, the software finds the intersecting points 304, 306 on each slide 300 (calibration slide) and corrects the actual position of the scanning stage 10 with the known deviation 308 that is stored in the associated calibration file for the slide 300 (calibration slide). The slide 300 (calibration slide) is uniquely allocated to the calibration file by reading the barcode 310 applied to each slide 300. In addition, each slide frame is identified using a discrete sticker with a barcode, since only the number of the slide frame and the number of the slide seat define the individual absolute slide position for a slide in this slide frame. The resulting calibration data are stored for all (e.g., up to 880 possible) slide seats or positions of a slide in the magazine.

| Reference list: | |
|---|---|
| 100 | Microscope scanning system |
| 2 | Magazine |
| 4, 210 | Slide frame |
| 6 | Robot module |
| 8 | Scanning microscope 8 |
| 10, 200 | Scanning stage |
| 202, 204 | Measuring device/motors for X, Y displacement |
| 212a-212h, 300 | Slide |
| 302 | Slide substrate |
| 304 | Calibration marking |
| 306 | Intersection point |
| 308 | Deviation |
| 310 | Storage medium |
| 312 | Transparent carrier material |

The invention claimed is:

1. A method for automatic calibration of slides, including the steps:
providing a calibrated slide frame with at least one slide seat, positioning coordinates for the slide seat being established for a microscope scanning system;
providing a non-calibrated slide with a calibration marking;
arranging the non-calibrated slide in a slide seat of the slide frame;
arranging the slide frame with the non-calibrated slide on a scanning stage of the microscope scanning system;
detecting marking coordinates of the calibration marking of the non-calibrated slide using the microscope scanning system;
detecting a deviation between the positioning coordinates for the slide seat and the marking coordinates of the non-calibrated slide; and
storing the detected deviation in a storage medium on the non-calibrated slide to form a calibrated slide.

2. A method in accordance with claim 1, the deviation including one or a plurality of deviation coordinates, the deviation coordinates establishing at least one of:
a maximum scannable scanning area for the slide, or
a center point for the slide, or
at least two reference points that establish a conversion of coordinates for the slide seat with respect to coordinates for the scanning stage for the microscope scanning system, or
a combination of two or more thereof.

3. A method in accordance with claim 1, the storage medium being a barcode or an RFID label.

4. A method in accordance with claim 1, the calibration marking including one or a plurality of lines or points or a combination thereof.

5. A method in accordance with claim 1, the calibration marking being applied to a transparent carrier material that is detachably connectable to the slide, the transparent carrier material preferably being an adhesive film.

6. A method in accordance with claim 1, the calibration marking being applied by printing on the slide or the transparent carrier material or a combination thereof.

7. A method in accordance with claim 1, the slide frame including a plurality of slide seats, and one slide with a calibration marking being placed into each slide seat in order to detect a deviation for each slide.

8. A method for automatic calibration of slide frames including the steps:
providing a slide frame having a plurality of slide seats, positioning coordinates of a slide seat being established;
providing a slide with a calibration marking;

arranging the slide in a slide seat of the slide frame;

arranging the slide frame with the slide on a scanning stage of a microscope scanning system;

detecting marking coordinates for the calibration marking for the slide based on detecting the calibration marking for the slide using the microscope scanning system;

detecting a deviation between the positioning coordinates of the slide seat and the marking coordinates of the slide;

establishing corrected positioning coordinates of the slide seat for of the slide frame based on the marking coordinates and the deviation; and storing the corrected positioning coordinates of the slide seat on a storage medium on the slide frame as a calibrated slide seat.

9. A method in accordance with claim 8, including the corrected positioning coordinates for the slide seat establishing at least one of:

a maximum scannable scanning area for a slide that may be arranged in the slide seat, or a center point for a slide that may be arranged in the slide seat, or at least two reference points that establish a conversion of coordinates of a slide that may be arranged in the slide seat with respect to coordinates of the scanning stage for the microscope scanning system; or a combination of two or more thereof.

10. A method in accordance with claim 8, the storage medium being a barcode or RFID label.

11. A method in accordance with claim 8, the calibration marking including one or a plurality of lines or points, or a combination thereof, and the deviation being stored in a storage medium, and the deviation being readable from this storage medium.

12. A method in accordance with claim 8, the slide frame including a plurality of slide seats, and a slide with a calibration marking being placed into each slide seat in order to establish corrected positioning coordinates for each slide seat.

13. The method of claim 1, wherein providing the slide frame includes:

holding the slide frame in a magazine; and an exchanger system automatically removing the slide frame from the magazine and positioning the slide frame on the scanning stage of the microscope scanning system.

14. The method of claim 1, wherein the slide frame includes a plurality of slide seats.

15. The method of claim 1, wherein the slide frame is a calibrated slide frame.

16. The method of claim 1, wherein the slide seat is a calibrated slide seat.

* * * * *

UNITED STATES PATENT AND TRADEMARK OFFICE
CERTIFICATE OF CORRECTION

| | | |
|---|---|---|
| PATENT NO. | : 9,243,934 B2 | Page 1 of 1 |
| APPLICATION NO. | : 13/847674 | |
| DATED | : January 26, 2016 | |
| INVENTOR(S) | : Thomas Loerch | |

It is certified that error appears in the above-identified patent and that said Letters Patent is hereby corrected as shown below:

In the Claims
Column 17, line 10, please delete the word "for".

Signed and Sealed this
Ninth Day of August, 2016

Michelle K. Lee
*Director of the United States Patent and Trademark Office*